United States Patent [19]

Chapuis

[11] Patent Number: 5,189,013

[45] Date of Patent: Feb. 23, 1993

[54] CAMPHOLENIC TERTIARY ALCOHOL AND ITS USE AS A PERFUMING INGREDIENT

[75] Inventor: Christian Chapuis, Mies, Switzerland

[73] Assignee: Firmenich S.A., Geneva, Switzerland

[21] Appl. No.: 839,603

[22] Filed: Feb. 21, 1992

[30] Foreign Application Priority Data

Mar. 22, 1991 [CH] Switzerland ............... 890/91 7

[51] Int. Cl.$^5$ ................................................ A61K 7/46
[52] U.S. Cl. ................................... 512/23; 568/367; 568/816
[58] Field of Search .................. 512/23; 568/367, 816

[56] References Cited

U.S. PATENT DOCUMENTS

| 4,173,585 | 11/1979 | Yoshida et al. | 568/816 |
| 4,188,310 | 2/1980 | Willis et al. | 568/816 |
| 4,278,569 | 7/1981 | Yoshida et al. | 568/816 |
| 4,289,658 | 9/1981 | Willis et al. | 568/816 |
| 5,087,707 | 2/1992 | Narula et al. | 568/816 |

OTHER PUBLICATIONS

Fieser et al, "Reagents for Organic Synthesis", pp. 415–421 (1967).

Primary Examiner—James H. Reamer
Attorney, Agent, or Firm—Pennie & Edmonds

[57] ABSTRACT 1,2-Dimethyl-4-(2',2',3'-trimethyl-3'-cyclopenten-1'-yl)-2-cyclohexen-1-ol is useful as a perfuming ingredient, for the preparation of perfuming compositions and perfumed articles to which it imparts woody-sandalwood type odor notes.

9 Claims, No Drawings

CAMPHOLENIC TERTIARY ALCOHOL AND ITS USE AS A PERFUMING INGREDIENT

BRIEF DESCRIPTION OF THE INVENTION

An object of the present invention is to provide 1,2-dimethyl-4-(2',2',3'-trimethyl-3'-cyclopenten-1'-yl)-2-cyclohexen-1-ol.

According to particular embodiments of the invention, the above-mentioned compound is provided in the form of an optically active isomer selected from the group consisting of:
a) (−)-(1'R)-cis-1,2-dimethyl-4-(2',2',3'-trimethyl-3'-cyclopenten-1'-yl)-2-cyclohexen-1-ol;
b) (−)-(1'R)-trans-1,2-dimethyl-4-(2',2',3'-trimethyl-3'-cyclopenten-1'-yl)-2-cyclohexen-1-ol;
c) (+)-(1'S)-cis-1,2-dimethyl-4-(2',2',3'-trimethyl-3'-cyclopenten-1'-yl)-2-cyclohexen-1-ol, and
d) (+)-(1'S)-trans-1,2-dimethyl-4-(2',2',3'-trimethyl-3'-cyclopenten-1'-yl)-2-cyclohexen-1-ol; or of an optically active mixture of two or more of said isomers.

Another object of the invention is a method to confer, improve, enhance or modify the odor properties of a perfuming composition or a perfumed article, which method comprises adding to said composition or article a fragrance effective amount of 1,2-dimethyl-4-(2',2',3'-trimethyl-3'-cyclopenten-1'-yl)-2-cyclohexen-1-ol.

The invention further concerns a perfuming composition or a perfumed article containing as an active perfuming ingredient 1,2-dimethyl-4-(2',2',3'-trimethyl-3'-cyclopenten-1'-yl)-2-cyclohexen-1-ol.

Finally, the invention also relates to a process for the preparation of 1,2-dimethyl-4-(2',2',3'-trimethyl-3'-cyclopenten-1'-yl)-2-cyclohexen-1-ol, comprising the reaction of 2-methyl-4-(2',2',3'-trimethyl-3'-cyclopenten-1'-yl)-2-cyclohexen-1-one with an appropriate Grignard reagent, under the conditions of a Grignard type reaction.

BACKGROUND OF THE INVENTION

The present invention relates to novel compounds which possess useful odor properties and, more particularly, it concerns a tertiary alcohol derived from campholenic aldehyde and the odor of which is of the sandalwood type.

The prior art in perfumery is rich in examples of compounds having a sandalwood odor. Nevertheless, the sandalwood-type odor still constitutes a fragrance field wherein the reasearch of new compounds remains very active. This results from the fact that natural sandalwood essential oil is a much appreciated perfuming ingredient, but very expensive and available in limited quantities. In addition, the reproduction of the odor of the natural ingredient is extremely difficult, even by admixture of known synthetic products. It is, in fact, observed that every prior art compound which is capable of imparting a sandalwood note to the compositions into which it is incorporated, only provides, on its own, a contribution towards the reproduction of one or the other of the particular characters of natural sandalwood oil, and this only to a certain extent. None of these compounds possesses an odor identical to that of any other and each of them can find a very specific use in perfumery, thus enriching the perfumer's palette in the domain of the sandalwood notes.

On the other hand, in spite of the rules established by a variety of researchers in order to define the relationship between the molecular structure and the sandalwood-type odor of the known compounds, rules designed to provide useful tools towards predicting the olfactive qualities of novel compounds on the basis of their molecular structure [see, for example, E. J. Brunke and E. Klein, Essential Oils, Ed. B. D. Mookherjee and C. J. Mussinan, page 83 and following, Allured Publishing Corp. (1981); R. E. Naipawer et al., ibid., page 105 and following; J. G. Witteveen et al., Recl. Trav. Chim. Pays-Bas 106, 29 (1987)], there can be no doubt that such rules establish structural requirements that, while seemingly essential, are by no means sufficient to make it possible to predict that a given molecular structure will imply, with certainty, a sandalwood odor, or, moreover, an odor of desirable quality, intensity and tenacity [see for example, J. G. Witteveen, cited reference, or yet, U.S. Pat. No. 4,501,341].

Therefore, the search for new compounds with sandalwood odor is evermore of actuality and the number of patents granted heretofore in this field, patents which recognize not only the novelty but also the inventive step of compounds whose structure is sometimes almost identical to that of prior known compounds, is a sure measure of the importance assigned to the discovery of new compounds of this type, the odor properties of which are undoubtedly advantageous over those of the previously described compounds.

The present invention provides a new solution to this problem.

THE INVENTION

The invention concerns, more particularly, a tertiary alcohol which is a derivative of campholenic aldehyde, i.e. 1,2-dimethyl-4-(2',2',3'-trimethyl3'-cyclopenten-1'-yl)-2-cyclohexen-1-ol.

It has been discovered that this compound possesses a powerful woody note, with a clear, very neat, sandalwood character which develops itself to become more powerful in the bottom note. It is, in fact, a very original note of excellent tenacity and which is also more powerful than that of most of the woody-sandalwood type compounds presently available on the market.

For example, when compared to (1'R,E)-3,3-dimethyl-5-(2',2',3'-trimethyl-3'-cyclopenten-1'-yl)-4-penten-2-ol, a product well appreciated by the perfumers and which is judged superior to many other commercial products with sandalwood odor [see, for example, EP 0 155 591], the compound of the present invention turns out to be of an easier use in composition, namely in fine perfumery applications. This results from the fact that, while possessing a slightly less powerful note than that of the cited known compound, the compound of the invention develops a cleaner and more natural sandalwood odor, which is also less animal than that of the cited prior art compound.

This olfactive superiority of 1,2-dimethyl-4-(2',2',3'-trimethyl-3'-cyclopenten-1'-yl)-2-cyclohexen-1-ol is totally surprising and unexpected if one considers its molecular structure. In fact, notwithstanding the high number of known sandalwood compounds which have a campholenic sub-structure, they are mostly primary or secondary alcohol derivatives of campholenic aldehyde and, to our knowledge, only two prior art documents disclose tertiary alcohols having useful odor properties [see U.S. Pat. No. 4,149,020 and U.S. Pat. No. 4,174,287], said tertiary alcohols being open chain campholenic derivatives.

When one analyzes the literature related to the compounds whose structure is closer to that of the compound according to the invention, i.e. whose structure is bicyclic, one realizes then that there are no examples of olfactively useful tertiary alcohols, in spite of the number of compounds disclosed. In this context, one can cite for example U.S. Pat. No. 4,173,585 which describes, amongst others, a mixture of compounds of formula

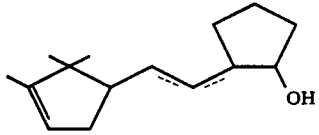
(Ia)

having a double bond in one of the positions indicated by the dotted lines, and a mixture of compounds of formula

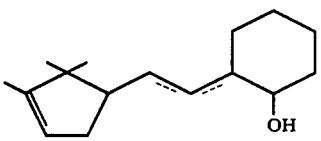
(Ib)

wherein the dotted lines have the meaning indicated above. These two mixtures possess, respectively, a woody-sandalwood odor, with a "cyclamal/Lilial®" character, and a sweet cedarwood, sandalwood odor.

German patent DE 29 35 683 describes compounds of formula

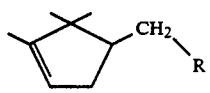
(II)

wherein symbol R represents a cyclic group of formula

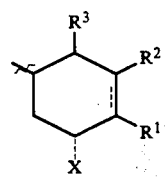

which can have an endocyclic double bond in the position indicated by the dotted line and wherein the exocyclic dotted line stands for a single bond, when X represents OH, or a double bond, X representing then an oxygen atom, and symbols $R^1$, $R^2$ and $R^3$ represent a hydrogen atom or a lower alkyl radical, or R represents a cyclic group of formula

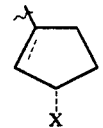

wherein the dotted lines and symbol X are defined as above. The compounds of formula (II) possess sandalwood notes of varied strength and character.

1,2-Dimethyl-4-(2',2',3'-trimethyl-3'-cyclopenten-1'-yl)-2-cyclohexen-1-ol according to the present invention belongs to a group of compounds whose molecular structure is more rigid than that of the cited known compounds of formula (I) or (II), while maintaining the distance which is judged to be optimum between the quaternary carbon atom 2' and the functional group 1. These are compounds that can be represented by the following basic skeleton

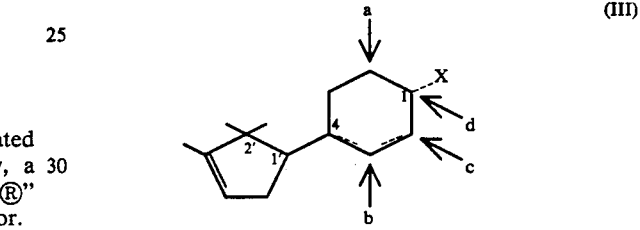
(III)

which can have a double bond in one of the endocyclic positions indicated by the dotted lines, the exocyclic dotted line representing a single bond when X is an OH radical and a double bond when X represents an oxygen atom. The six-membered ring may possess ore or more substituent methyl groups in positions a, b, c and d.

In view of the prior art, one might have expected that the increased rigidity of the cyclic chain containing the functional group would have had a more or less uniform effect over a group of compounds having the same basic skeleton (III) and that it would have brought about, by reducing the number of possible conformations of said cyclic chain, an improvement in the olfactive properties, relative to those of the known compounds. Yet, we have now discovered that, unlike what could have been predicted, amongst a good number of compounds having structure (III), some of which are reported here, only 1,2-dimethyl-4-(2',2',3'-trimethyl-3'-cyclopenten-1'-yl)-2-cyclohexen-1-ol possesses odor properties which are superior to those of the known compounds and an odor whose character best resembles that of natural sandalwood. As can be seen in the table presented hereinafter, there are other compounds with structure (III) which have sandalwood-type notes, but which are either too weak, or qualitatively less useful.

TABLE I

| Compounds | Odor properties |
|---|---|
| | cumin, animal, woody, slightly sandalwood |

TABLE I-continued

| Compounds | Odor properties |
|---|---|
| [structure] | sesquiterpenes, fruity, weak |
| [structure] | woody, floral, sandalwood, vague |
| [structure] (cis) | woody-weak, very slightly sandalwood, fruity |
| [structure] | woody, phenolic, leather, slightly sandalwood |
| [structure] OH (cis:trans) (42:52) | slightly sandalwood, weak |
| [structure] | weak |
| [structure] | weak, floral, dirty |
| [structure] | floral, woody, vaguely sandalwood, weak |
| [structure] | iris, slightly sandalwood |
| [structure] | weak, vaguely floral, very vaguely sandalwood |
| [structure] | woody, vaguely sandalwood |

In view of this table, the olfactive quality of the compound of the invention is all the more surprising, since compounds having an almost identical structure exhibit olfactive characters which are not very distinctive, are too weak or which do not contain the desired sandalwood note.

This was also observed when the odor properties of the instant compound were compared with those of known compounds, having a close structure, and obeying formulae (Ib) and (II) previously cited. For example, (-)-(1'R)-2-[2-(2',2',3'-trimethyl-3'-cyclopenten-1'-yl)ethylidene]-1-cyclohexanol of formula

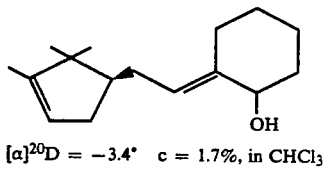

$[\alpha]^{20}D = -3.4°$  c = 1.7%, in CHCl$_3$ which was prepared as described in U.S. Pat. No. 4,173,585, but from a pure optically active starting product, possesses a weakly woody, resinous odor, with a very slight, sandalwood character. Likewise, (+)-(1'S)-3-(2',2',3'-trimethyl-3'-cyclopenten-1'-yl)methyl-1-cyclohexanol and (+)-(1'R)-4-methyl-3-(2',2',3'-trimethyl-3'-cyclopenten-1'-yl)methyl-1-cyclohexanol of formula

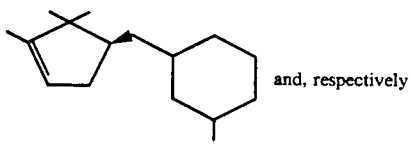

and, respectively $[\alpha]^{20}D = +9.3°$  c = 2.95%, in CHCl$_3$

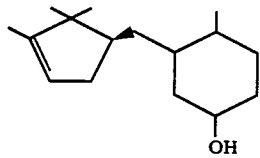

$[\alpha]^{20}D = +0.2°$  c = 2.25%, in CHCl$_3$ obtained according to DE 29 35 683 but using pure optically active starting products, turned out to have a vaguely woody-sandalwood odor, without character and, respectively a vaguely sandalwood odor, even weaker than that of the preceding one.

As a result of its olfactive properties, 1,2-dimethyl-4-(2',2',3'-trimethyl-3'-cyclopenten-1'-yl)-2-cyclohexen-1-ol is particularly advantageous for fine perfumery applications, for the preparation of perfumes and colognes of varied nature, namely of the woody-floral-oriental type, compositions to which it imparts a clear sandalwood character, while exalting the floral and animal aspect of the composition.

The tenacity of its odor note renders the compound of the invention equally useful in technical perfumery, namely for perfuming detergents and fabric softeners. Other products which can be advantageously perfumed by means of the compound of the invention include soaps, shower and bath gels, shampoos, cosmetic preparations, body or air deodorants or household products.

As it is often the case in perfumery, the compound can be used, as a perfuming ingredient, either alone or in admixture with other perfuming coingredients, solvents or adjuvants of current use.

The concentrations in which the compound of the invention can be used for the above-mentioned applications vary in a wide range of values, which is a function, amongst other parameters, of the nature of the product to be perfumed and of the desired perfuming effect. By way of example, concentrations of the order of 1 to 10% by weight, or even more, can be cited when the compound is used in perfuming bases and concentrates. Considerably lower concentration values than those cited can be employed when the compound is used for perfuming the variety of articles mentioned above.

It should be noted that the compound according to the invention can take several optically active forms, as a result of the plurality of chiral centers in the molecule. As is described below, these several isomers can be prepared by using appropriate optically active forms of the starting products. It was observed that the isomers thus obtained were all olfactively distinct from each other, both as regards the character and the strength of their sandalwood note. Generally, however, it was observed that these differences were not very marked and that all the compounds, as well as their mixtures, were equally convenient for the perfumery applications according to the invention. There was, nevertheless, a perfumers' preference for the isomers of (−)-(1'R) configuration and, amongst these, for (−)-(1'R)-cis-1,2-dimethyl-4-(2',2',3'-trimethyl-3'-cyclopenten-1'-yl)2-cyclohexen-1-ol.

When reference is made in the present specification to 1,2-dimethyl-4-(2',2',3'-trimethyl-3'-cyclopenten-1'-yl)-2-cyclohexen-1-ol, it is meant as a reference to any one of its optically active isomers, or to any mixture of the latter.

The invention has also as its object a process for the preparation of 1,2-dimethyl-4-(2',2',3'-trimethyl-3'-cyclopenten-1'-yl)-2-cyclohexen-1-ol, which process comprises the reaction of 2-methyl-4-(2',2',3'-trimethyl-3'-cyclopenten-1'-yl)-2-cyclohexen-1-one with an appropriate Grignard reagent, under the usual conditions of this type of reaction. The starting cyclohexenone in the process of the invention can take several optically active stereoisomer forms and, obviously, the latter determine the configuration of the final product.

2-Methyl-4-(2',2',3'-trimethyl-3'-cyclopenten-1'-yl)-2-cyclohexen-1-one, in the desired configuration, or in the form of a mixture of diastereomers, can be obtained from the appropriate stereoisomer form of campholenic aldehyde, by means of conventional reactions, such as illustrated in the following reaction scheme. In the latter, the above-mentioned cyclohexenone is represented, in the form of the 1'R (mixture of 4R/4S diastereomers) configuration isomer, by number 6 and the compound according to the invention, in the corresponding configuration, is indicated by number 22.

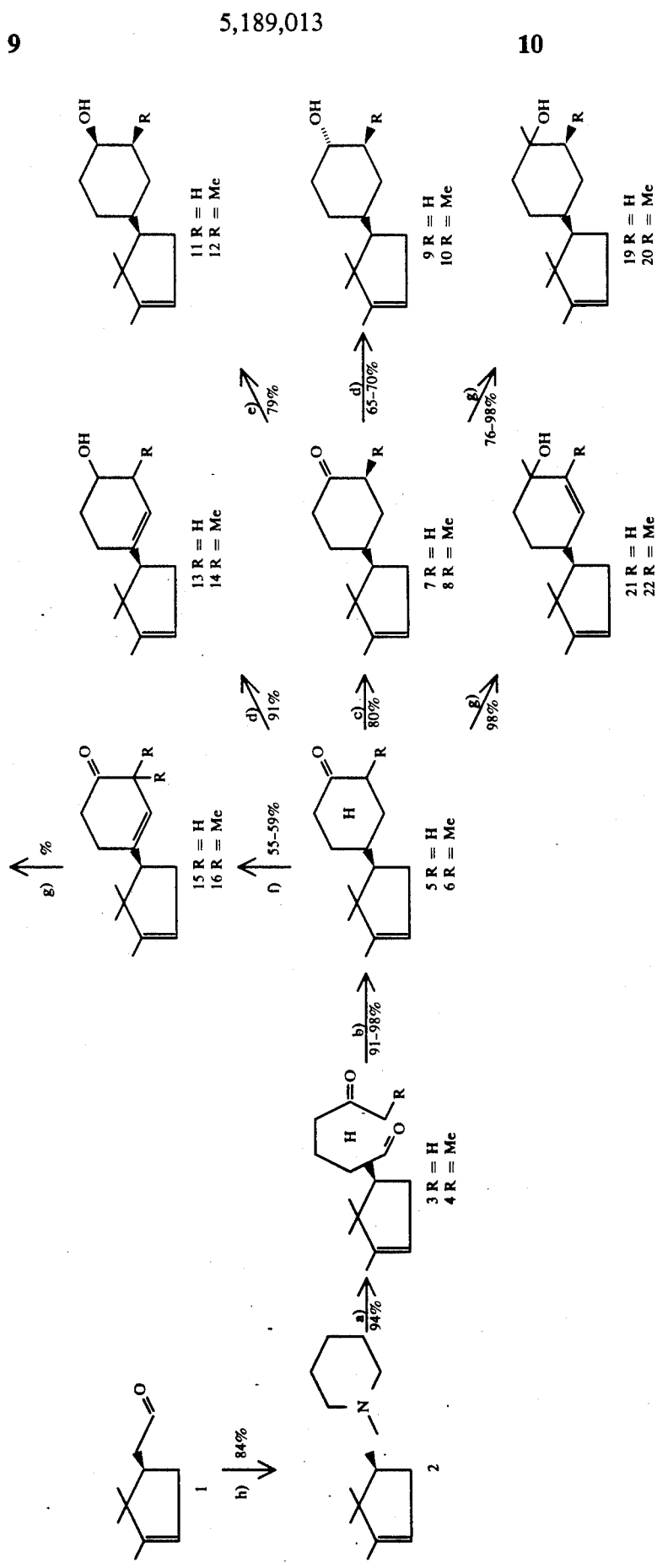

-continued
Scheme b) pTsOH, cyclohexane
c) H₂/Raney Ni, EtOH
d) LiAlH₄, Et₂O
e) L-Selectride, THF -70°
f) DMSO, KOtBu, RI
g) MeMgI, ether
h) piperidine, H⊕, toluene This scheme also illustrates the conventional type reactions which enable the preparation, starting from the same cyclohexenone, of many compounds obeying the basic structure (III), namely those cited in Table I.

The process according to the invention will now be described in greater detail by way of the examples presented hereinafter, wherein the temperatures are indicated in degrees centigrade and the abbreviations have the usual meaning in the art.

Other examples, presented further on, illustrate perfumery applications of the compound according to the invention.

EXAMPLE 1

Preparation of
(−)-(1'R)-cis-1,2-dimethyl-4-(2',2',3'-trimethyl-3'-cyclopenten-1'-yl)-2-cyclohexen-1-ol and of
(−)-(1'R)-trans-1,2-dimethyl-4-(2',2',3'-trimethyl-3'-cyclopenten-1'-yl)-2-cyclohexen-1-ol a) Preparation of
(+)-(1'R,E)-N-[2-(2',2',3'-trimethyl-3'-cyclopenten-1'-yl) ethenyl] piperidine A 3 l flask was charged with 608 g (4 mol) of (+) campholenic aldehyde, 2 l of toluene, 408 g (4.8 mol) of piperidine and 3 g of p-toluenesulfonic acid. The mixture was heated to reflux in the presence of a water separator. At room temperature, there were added 3 g of $Na_2CO_3$ and then, after 15 min, the reaction mixture was filtered and evaporated to yield 921 g of an oil which was distilled to provide 733.87 g of the desired piperidine.

B.p 136°-138°/4 Pa; yield: 84%.
$[\alpha]^{20}_D = +13.6°$ c=2.22%, in $CHCl_3$.
IR: 2940, 1640, 1450, 1380, 1190 cm$^{-1}$.
NMR($^1$H, 360 MHz): 0.75(s, 3H); 0.92(s, 3H); 1.61(d, J=2 Hz, 3H); 2.77(t, J=7 Hz, 4H); 4.42(dxd, $J_1$=15 Hz, $J_2$=8 Hz, 1H); 5.24(s, 1H); 5.82(d, J=15 Hz, 1H) δ ppm.
MS: 219(M+, 64), 204(100), 176(20), 134(44), 122(85), 111(68), 96(60), 91(50), 84(56), 79(55), 41(68).

b) Preparation of
(+)-(1'R)-5-oxo-2-(2',2',3'-trimethyl-3'-cyclopenten-1'-yl)heptanal In a 250 ml flask, there were charged, under $N_2$, 36.5 g (0.167 mol) of the piperidine prepared according to a), in 70 ml of cyclohexane. Under stirring, 16.9 g (0.2 mol) of ethyl vinylketone were added and the mixture was brought to reflux for 24 h. 25 Ml of 50% acetic acid were added at room temperature and the mixture was taken to reflux for 15 min. After separating the phases, the organic phase was washed 3 times with 15% HCl, twice with water, twice with saturated NaCl to yield, after drying ($Na_2SO_4$) and evaporation, 39.28 g of product. After distillation, 36.92 g of the desired heptanal were obtained, under the form of 4:3 mixture of diastereomers. This diastereomer mixture cannot be separated by simple separation techniques and was used as such in the next step of the synthesis.

B. p. 103°-118°/4 Pa; yield: 94%.
$[\alpha]^{20}_D = +5.86°$ c=3.68%, in $CHCl_3$.
IR: 2950, 1720, 1460, 1360, 1120, 1020 cm$^{-1}$.
NMR($^1$H, 360 MHz): major isomer: 0.83(s, 3H); 0.96(s, 3H); 1.04(t, J=7 Hz, 3H); 1.59(s, 3H); 5.24(s, 1H); 9.52(d, J=4 Hz, 1H) δ ppm minor isomer: 0.94(s, 3H); 1.05(t, J=7 Hz, 3H); 1.11(s, 3H); 1.58(s, 3H); 5.21(s, 1H); 9.55(d, J=4 Hz, 1H) δ ppm.
NMR($^{13}$C): major isomer: 7.77(q); 12.49(q); 20.15(q); 21.79(t); 22.89(q); 33.77(t); 36.11(t); 39.31(t); 46.99(s); 50.13(d); 53.8(d); 121.12(d); 148.55(s); 205.48(d); 210.39(s) δ ppm minor isomer: 7.77(q); 12.4(q); 20.22(q); 22.58(t); 27.16(q); 32.93(t); 36.4(t); 39.55(t); 47.7(s); 51.1(d); 52.78(d); 121.45(d); 148.5(s); 204.7(d); 210.47(s) δ ppm.
MS: 236(M+, 0), 121(12), 108(100), 93(65), 57(22).
Odor: sesquiterpenes, weak c) Preparation of
(−)-(1'R)-2-methyl-4-(2',2',3'-trimethyl-3'-cyclopenten-1'-yl)-2-cyclohexen-1-one A mixture of 26 g (0.11 mol) of the heptanal prepared according to b), 1 g of p-toluenesulfonic acid and 50 ml of cyclohexane was heated to reflux for 4 h, in a 100 ml flask equipped with a water separator. The reaction mixture was washed twice with $NaHCO_3$, twice with $H_2O$ and twice with saturated NaCl. After drying over $Na_2SO_4$, evaporation provided 25.26 g of product, which was distilled to yield 21.79 g of the desired cyclohexenone in the form of a 1.1:1 mixture of diastereomers.

B. p. 130°/13 Pa; yield: 91%.
$[\alpha]^{20}_D = -14.6°$ c=3.63%, in $CHCl_3$.
IR: 3020, 2950, 1695, 1450, 1360, 900, 800 cm$^{-1}$.
NMR($^1$H, 360 MHz): major diastereomer: 0.98(s, 3H); 1.12(s, 3H); 1.61(s, 3H); 1.80(s, 3H); 5.24(s, 1H); 6.9(s, 1H) δ ppm minor diastereomer: 0.96(s, 3H); 1.1(s, 3H); 1.61(s, 3H); 1.77(s, 3H); 5.24(s, 1H); 6.73(s, 1H) δ ppm.
NMR($^{13}$C): major diastereomer: 12.5(q); 19.18(q); 20.03(q); 27.64(q); 28.35(t); 34.75(t); 36.44(t); 37.75(d); 46.92(s); 54(d); 121.2(d); 134.7(s); 148.55(s); 149.84(d); 199.75(s) δ ppm minor diastereomer: 12.5(q); 16.18(q); 19.78(q); 27.35(q); 29.53(t); 34.18(t); 37.04(t); 38.09(d); 47(s); 53.09(d); 121.35(d); 135.3(s); 148.5(s); 149.62(d); 199.75(s) δ ppm.
MS: 218(M+, 5), 203(8), 189(21), 109(100), 95(50), 81(62), 67(77).
Odor: sesquiterpenes, fruity, weak.

d) A 250 ml flask, under $N_2$, was charged with 0.96 g (0.004 mol) of Mg and 50 ml of ether, to which 5.68 g (0.04 mol) of $CH_3I$ were added dropwise, and then, after all the Mg had vanished, a solution of 6.5 g (0.03 mol) of the cyclohexenone prepared in c) in 20 ml of ether was added over 20 min. The mixture was heated to reflux for 1 h. A saturated solution of $NH_4Cl$ (30 ml) was added thereto, followed by extraction with 4×10 ml of ether, washing with water and then a saturated solution of NaCl, drying over $Na_2SO_4$ and evaporating to yield 7.43 g of a mixture 1:2 of cis:trans isomers of (1'R)-1,2-dimethyl-4-(2',2',3'-trimethyl-3'-cyclopenten-1'-yl)-2-cyclohexen-1-ol. This mixture was chromatographed on a $SiO_2$ column, using a mixture of 8:2 toluene/ethyl acetate as eluting agent, to yield 2.1 g of the cis isomer, in the form of a 1.6:1 mixture of diastereomers, and 3.8 g of the trans isomer, in the form of a 1.1:1 mixture of diastereomers.

B. p. 160°-180°/13 Pa; yield: 98%

(−)-(1'R)-cis-1,2-dimethyl-4-(2',2',3'-trimethyl-3'-cyclopenten-1'-yl)-2-cyclohexen-1-ol $[\alpha]^{20}_D = -12.3°$ c=3.05%, in $CHCl_3$.
IR: 3400, 2940, 1440, 1360, 940, 915, 805 cm$^{-1}$.
NMR($^1$H, 360 MHz): major diastereomer: 0.92(s, 3H); 1.13(s, 3H); 1.29(s, 3H); 1.59(s, 3H); 1.77(s, 3H); 5.22(s, 1H); 5.64(s, 1H) δ ppm minor diastereomer:

0.90(s, 3H); 1.08(s, 3H); 1.29(s, 3H); 1.59(s, 3H); 1.77(s, 3H); 5.22(s, 1H); 5.45(s, 1H) δ ppm.

NMR($^{13}$C): major diastereomer: 12.5(q); 18.19(q); 19.86(q); 25.04(t); 27.13(q); 27.91(q); 34.62(t); 38.06(d); 38.48(t); 46.98(s); 54.57(d); 69.65(s); 121.38(d); 129.77(d); 137.52(s); 148.67(s) δ ppm minor diastereomer: 12.5(q); 18.19(q); 19.58(q); 26.13(t); 27.37(q); 27.91(q); 34.34(t); 38.11(d); 38.63(t); 47.22(s); 54.27(d); 69.44(s); 121.48(d); 129.47(d); 137.86(s); 148.67(s) δ ppm.

MS: 220(M+, 0), 216(8), 108(100), 91(53), 67(48), 43(35).

(−)-(1′R)-trans-1,2-dimethyl-4-(2′,2′,3′-trimethyl-3′-cyclopenten-1′-yl)-2-cyclohexen-1-ol $[\alpha]^{20}_D = -12.6°$ c=3.2%, in CHCl$_3$.
IR: 3400, 2950, 1440, 1360, 1110 cm$^{-1}$.
NMR($^1$H, 360 MHz): major diastereomer: 0.92(s, 3H); 1.09(s, 3H); 1.3(s, 3H); 1.59(s, 3H); 1.76(s, 3H); 5.22(s, 1H); 5.59(s, 1H) δ ppm minor diastereomer: 0.89(s, 3H); 1.06(s, 3H); 1.29(s, 3H); 1.59(s, 3H); 1.64(s, 3H); 5.22(s, 1H); 5.38(s, 1H) δ ppm.

NMR($^{13}$C): major diastereomer: 12.5(q); 17.68(q); 19.75(q); 26.0(t); 26.8(q); 27.34(q); 34.31(t); 37.51(d); 38.86(t); 47.22(s); 54.2(d); 70.92(s); 121.55(d); 128.19(d); 138.61(s); 148.52(s) δ ppm minor diastereomer: 12.5(q); 17.68(q); 19.61(q); 26.86(q); 27.49(t); 27.64(q); 34.57(t); 37.41(d); 38.35(t); 46.88(s); 54.49(d); 71.17(s); 121.25(d); 128.67(d); 138.02(s); 148.85(s) δ ppm.

MS: minor diastereomer: 234(M+, 3), 216(13), 109(100), 91(57), 67(65), 43(80). major diastereomer: 234(M+, 8), 216(9), 201(10), 109(100), 91(50), 67(54), 43(72).

EXAMPLE 2

Preparation of
(+)-(1′S)-cis-1,2-dimethyl-4-(2′,2′,3′-trimethyl-3′-cyclopenten-1′-yl)-2-cyclohexen-1-ol and of
(+)-(1′S)-trans-1,2-dimethyl-4-(2′,2′,3′-trimethyl-3′-cyclopenten-1′-yl)-2-cyclohexen-1-ol These compounds were prepared in an identical manner to that described in Example 1, but using as starting product (−) campholenic aldehyde for the preparation of (−)-(1′S,E)-N-[2-(2′,2′,3′-trimethyl-3′-cyclopenten-1′-yl)ethenyl] piperidine. The analytical data of the obtained intermediate and final products were identical to those of their corresponding enantiomers described in Example 1, with the exception of the optical rotation angles, which were as follows:

a) (−)-(1′S,E)-N-[2-(2′,2′,3′-trimethyl-3′-cyclopenten-1′-yl)ethenyl]piperidine
$[\alpha]_D^{20} = -18.77°$ (pure)
b) (−)-(1′S)-5-oxo-2-(2′,2′,3′-trimethyl-3′-cyclopenten-1′-yl)heptanal
(mixture of diastereomers)
$[\alpha]_D^{20} = -6.23°$ c = 3.75%, in CHCl$_3$
c) (+)-(1′S)-2-methyl-4-(2′,2′,3′-trimethyl-3′-cyclopenten-1′-yl)-2-cyclohexen-1-one (mixture of diastereomers)
$[\alpha]_D^{20} = +20.4°$ (pure)
d) (+)-(1′S)-cis-1,2-dimethyl-4-(2′,2′,3′-trimethyl-3′-cyclopenten-1′-yl)-2-cyclohexen-1-ol
(mixture of diastereomers)
$[\alpha]_D^{20} = +15.3°$ c = 1.67%, in CHCl$_3$
e) (+)-(1′S)-trans-1,2-dimethyl-4-(2′,2′,3′-trimethyl-3′-cyclopenten-1′-yl)-2-cyclohexen-1-ol
(mixture of diastereomers)
$[\alpha]_D^{20} = +28.95°$ c = 1.18%, in CHCl$_3$

EXAMPLE 3

Preparation of a Perfuming Composition

A base perfuming composition, intended for a feminine cologne, was prepared by admixing the following ingredients:

| Ingredients | Parts by weight |
|---|---|
| Benzyl acetate | 80 |
| Geranyl acetate | 20 |
| Styrallyl acetate | 20 |
| Hexylcinnamic aldehyde | 100 |
| 10%* Amyl allyl glycolate | 150 |
| 10%* γ-Undecalactone | 100 |
| Bergamot essential oil | 500 |
| Citronellol | 50 |
| Coumarin | 150 |
| Exaltolide ®[1] | 200 |
| Isoeugenol | 25 |
| Jasmin absolute | 75 |
| Iralia ®[2] | 600 |
| Muscone | 100 |
| Hedione ®[3] | 1220 |
| Eugenol | 50 |
| Benzyl salicylate | 100 |
| cis-3-Hexenol salicylate | 60 |
| Sandalwood essential oil | 900 |
| Vanillin | 100 |
| Ylang essential oil | 150 |
| Sicily lemon essential oil | 50 |
| Total | 4800 |

*in dipropyleneglycol (DIPG)
[1]cyclopentadecanolide; origin: Firmenich SA, Geneva, Switzerland
[2]methylionone (isomeric mixture); origin: Firmenich SA, Geneva, Switzerland
[3]methyl dihydrojasmonate; origin: Firmenich SA, Geneva, Switzerland To this base composition of the floral-oriental-sandalwood type, there were added 200 parts by weight of 1,2-dimethyl-4-(2′,2′,3′-trimethyl-3′-cyclopenten-1′-yl)-2-cyclohexen-1-ol. A new composition was thus obtained, the odor note of which had become distinctly more sandalwood, rounder and with more lift. In addition, the floral and musky notes of the base composition were exalted in the new composition, as a result of the adjunction of the above-mentioned compound. This enhancing effect of the sandalwood character of the composition, through adding the compound of the invention, was very clear. Thus, it was observed that, if instead of adding said compound, the quantity of sandalwood essential oil in the base composition was doubled, then the note of this composition became flat, sweetish, without character. The exaltation of the woody-floral character of the composition, so remarked when 1,2-dimethyl-4-(2′,2′,3′-trimethyl-3′-cyclopenten-1′-yl)-2-cyclohexen-1-ol was added to the base composition, was not observed either.

EXAMPLE 4

Preparation of a Perfuming Composition

A base perfuming composition, intended for a fabric softener, was prepared by admixture of the following ingredients:

| Ingredients | Parts by weight |
|---|---|
| Benzyl acetate | 5 |
| Carbinol acetate | 3 |
| 10%* Redistilled anisic aldehyde | 5 |
| Hexylcinnamic aldehyde | 5 |
| 10%* Methyl benzoate | 3 |
| Citronellol | 5 |
| Verdyl acetate | 3 |

-continued

| Ingredients | Parts by weight |
| --- | --- |
| p-tert-Butylcyclohexyl acetate | 7 |
| 1%* Ethyl vanillin | 3 |
| Galaxolide ®[1] 50 | 7 |
| Geraniol | 5 |
| Isoraldeine ®[2] 70 | 3 |
| Lilial ®[3] | 5 |
| Linalol | 4 |
| Lyral ®[4] | 2 |
| Cryst. methylnaphthylketone | 1 |
| 1%* Octyne methyl carbonate | 4 |
| Phenethylol | 10 |
| Rosinol | 3 |
| Benzyl salicylate | 5 |
| Cedroxyde ®[5] | 5 |
| Amyl salicylate | 6 |
| Total | 99 |

*in dipropyleneglycol (DIPG)
[1] 1,3,4,6,7,8-hexahydro-4,6,6,7,8,8-hexamethyl-cyclopenta[g]isochromene; origin: IFF Inc., USA
[2] iso-methylionone; origin: L. Givaudan, Vernier, Switzerland
[3] 3-(4-tert-butyl-1-phenyl)-2-methylpropanal; origin: L. Givaudan, Vernier, Switzerland
[4] 4-(4-hydroxy-4-methylpentyl)-3-cyclohexen-1-carboxaldehyde; origin: IFF Inc., USA
[5] trimethyl cyclododecatriene epoxyde; origin: Firmenich SA, Geneva, Switzerland To this base composition of the floral-rosy, musky type, there was added 1 part by weight of 1,2-dimethyl-4-(2',2',3'-trimethyl-3'-cyclopenten-1'-yl)-2-cyclohexen-1-ol. A new composition was thus obtained, the olfactive note of which, although it had not changed radically relative to that of the base composition, had become warmer, with a distinctly perceptible woody undernote. It was observed that this odor effect was even more perceptible on wet linen, freshly out of the washing machine, and that it was far longerlasting on dried linen, thus showing the excellent substantivity of the odor note imparted by the above-mentioned compound of the invention.

What I claim is:

1. 1,2-Dimethyl-4-(2',2',3'-trimethyl-3'-cyclopenten-1'-yl)-2-cyclohexen-1-ol.

2. An optically active compound selected from the group consisting of:
   a) (−)-(1'R)-cis-1,2-dimethyl-4-(2',2',3'-trimethyl-3'-cyclopenten-1'-yl)-2-cyclohexen-1-ol;
   b) (−)-(1'R)-trans-1,2-dimethyl-4-(2',2',3'-trimethyl-3'-cyclopenten-1'-yl)-2-cyclohexen-1-ol;
   c) (+)-(1'S)-cis-1,2-dimethyl-4-(2',2',3'-trimethyl-3'-cyclopenten-1'-yl)-2-cyclohexen-1-ol, and
   d) (+)-(1'S)-trans-1,2-dimethyl-4-(2',2',3'-trimethyl-3'-cyclopenten-1'-yl)-2-cyclohexen-1-ol.

3. An optically active mixture of any two or more compounds according to claim 2.

4. A method to confer, improve, enhance or modify the odor properties of a perfuming composition or a perfumed article, which method comprises adding to said composition or article a fragrance effective amount of 1,2-dimethyl-4-(2',2',3'-trimethyl-3'-cyclopenten-1'-yl)-2-cyclohexen-1-ol.

5. A method according to claim 4, wherein 1,2-dimethyl-4-(2',2',3'-trimethyl-3'-cyclopenten-1'-yl)-2-cyclohexen-1-ol is added in the form of any one of its optically active isomers defined in claim 2, or in the form of a mixture according to claim 3.

6. A perfuming composition or a perfumed article containing as an active perfuming ingredient 1,2-dimethyl-4-(2',2',3'-trimethyl-3'-cyclopenten-1'-yl)-2-cyclohexen-1-ol.

7. A perfuming composition or a perfumed article according to claim 6, wherein 1,2-dimethyl-4-(2',2',3'-trimethyl-3'-cyclopenten-1'-yl)-2-cyclohexen-1-ol is present in the form of any one of its optically active isomers defined in claim 2, or in the form of a mixture according to claim 3.

8. A perfumed article according to claim 6, in the form of a perfume or a cologne, a shower or bath gel, a shampoo, a cosmetic preparation, an air or body deodorant, a detergent or a fabric softener, or a household product.

9. 2-Methyl-4-(2',2',3'-trimethyl-3'-cyclopenten-1'-yl)-2-cyclohexen-1-one.

* * * * *

UNITED STATES PATENT AND TRADEMARK OFFICE
CERTIFICATE OF CORRECTION

PATENT NO. : 5,189,013
DATED : Feb. 23, 1993
INVENTOR(S) : Christian Chapuis

It is certified that error appears in the above-indentified patent and that said Letters Patent is hereby corrected as shown below:

Columns 3,4 and 5, the formulas of Table I, should read :

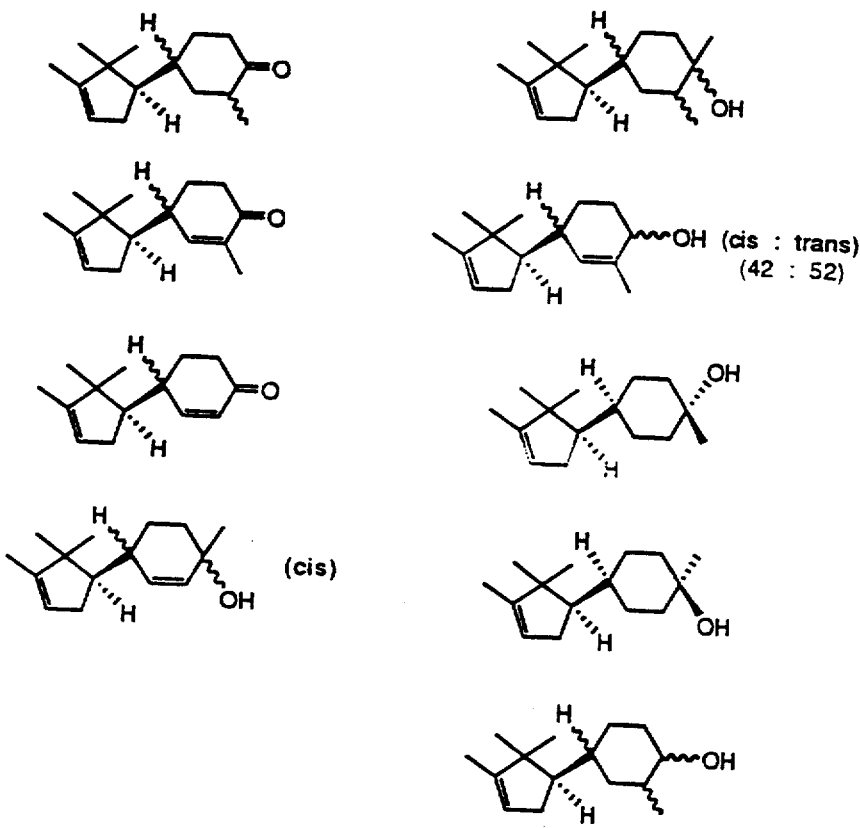

UNITED STATES PATENT AND TRADEMARK OFFICE
CERTIFICATE OF CORRECTION

PATENT NO. : 5,189,013
DATED : Feb. 23, 1993
INVENTOR(S) : Christian Chapuis

It is certified that error appears in the above-indentified patent and that said Letters Patent is hereby corrected as shown below:

Table I (continued)

Compounds

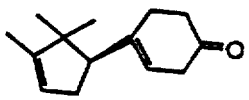

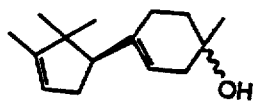

UNITED STATES PATENT AND TRADEMARK OFFICE
CERTIFICATE OF CORRECTION

PATENT NO. : 5,189,013
DATED : Feb. 23, 1993
INVENTOR(S) : Christian Chapuis

It is certified that error appears in the above-indentified patent and that said Letters Patent is hereby corrected as shown below: Columns 9,10 and 11, the formulas should read :

Scheme

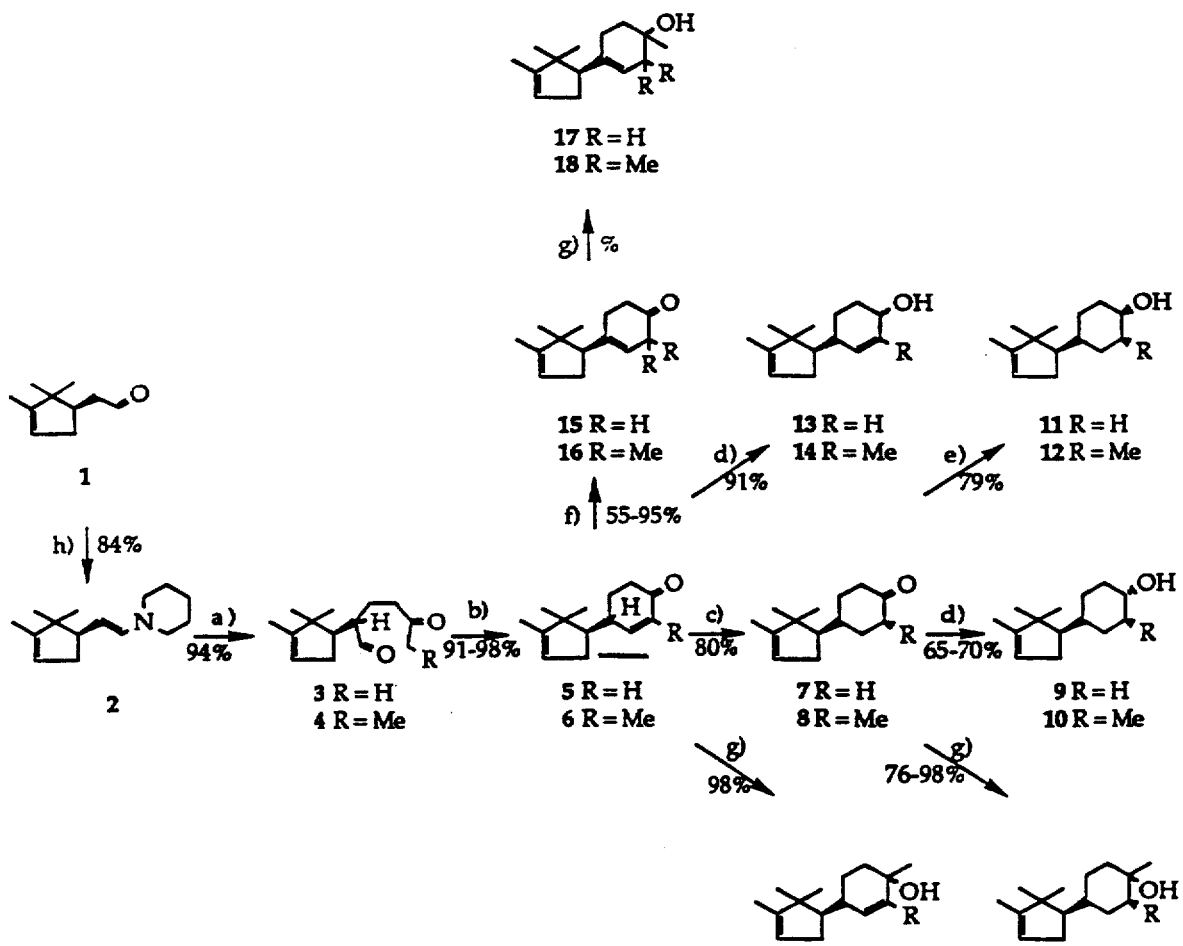

UNITED STATES PATENT AND TRADEMARK OFFICE
CERTIFICATE OF CORRECTION

PATENT NO. : 5,189,013
DATED : Feb. 23, 1993
INVENTOR(S) : Christian Chapuis

It is certified that error appears in the above-indentified patent and that said Letters Patent is hereby corrected as shown below:

21 R = H
22 R = Me

19 R = H
20 R = Me a)  R, cyclohexane ⇌ , AcOH
b) pTsOH, cyclohexane ⇌
c) H$_2$/Raney Ni, EtOH
d) LiAlH$_4$, Et$_2$O e) L-Selectride, THF -70°
f) DMSO, KOtBu, RI
g) MeMgI, ether ⇌
h) piperidine, H$^{\oplus}$, toluene Signed and Sealed this Eighth Day of August, 1995

Attest:

BRUCE LEHMAN

*Attesting Officer*  *Commissioner of Patents and Trademarks*